United States Patent [19]
Cauwenbergh

[11] Patent Number: 6,099,870
[45] Date of Patent: *Aug. 8, 2000

[54] METHODS FOR IMPROVING THE HEALTH OF HAIR AND SCALP

[75] Inventor: Gerard F. Cauwenbergh, Plainsboro, N.J.

[73] Assignee: Johnson & Johnson Consumer Companies, Inc., Skillman, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 09/208,948

[22] Filed: Dec. 9, 1998

Related U.S. Application Data

[60] Provisional application No. 60/069,993, Dec. 18, 1997.

[51] Int. Cl.[7] .......................... A61K 33/04; A61K 33/00; A61K 31/555; A61K 31/415
[52] U.S. Cl. .......................... 424/702; 424/722; 514/188; 514/399
[58] Field of Search ..................................... 424/702, 722; 514/188, 399

[56] References Cited

U.S. PATENT DOCUMENTS

| | | |
|---|---|---|
| 4,942,162 | 7/1990 | Rosenberg et al. . |
| 5,270,035 | 12/1993 | Chimento .................................. 424/70 |
| 5,456,851 | 10/1995 | Liu et al. . |
| 5,639,459 | 6/1997 | Bouras .................................. 424/195.1 |
| 5,650,145 | 7/1997 | Saint-Leger ........................... 424/70.1 |
| 5,702,691 | 12/1997 | Ichinose et al. ....................... 424/70.1 |
| 5,760,043 | 6/1998 | Dufetel et al. ........................... 514/272 |

FOREIGN PATENT DOCUMENTS

| | | |
|---|---|---|
| 1295276 | 11/1972 | United Kingdom . |
| WO 9629045 | 9/1996 | WIPO . |
| WO 9629983 | 10/1996 | WIPO . |

OTHER PUBLICATIONS

Rushton, D.H., et al., "Natural Progression of Male Pattern Baldness in Young Men", 16 Clin. Exp. Dermatol. 188–192 (1991).

Bergfeld, F.W., "Hair Disorders" Dermatology 1541–1560 (1992).

Pierard–Franchimont, C., et al., Approche Physio-pathologique de la Seborrhee Du Cuir Chevelu:, 115 Ann. Dermatol. Venereol. 451–53 (1988). ["Pierard"].

English abstract—Van Vloten.

English abstract—Pierard.

English abstract—Sabouraud.

Dawber, P., "The Scaly and Itchy Scalp", *Hair and Scalp Disorders* 191–227 (1995).

Ford, G.P., et al., 111 Br. J. Dermatol 603–07 (1984) ("Ford").

Sabouraud, R., "Maladies Due Cuir Chevelu II", Les Maladies Desquamatives, 207–327 (1904) ["Sabouraud"].

Van Vloten, W., et al., "Eczeem", 8 Dermatologie and Venerologie 90–109 (1966) ["Van Vloten"].

Arrese, J., et al., "Effect of Ketoconazole Medicated Shampoos on Squamometry and *Malassezia Ovalis* Load in *Pityriasis Capitis*", 58 Cutis 235–37 (1996).

Shuster, S., "Psoriatic Alopecia", 87 Br. J. Dermatol. 74–77 (1972).

*Primary Examiner*—Raymond Henley, III
*Attorney, Agent, or Firm*—Michele G. Mangini

[57] ABSTRACT

A method of increasing the amount of anagen hair in a human comprising applying an azole or zinc pyrithione, or mixtures thereof to an area of a human where an increase in the amount of anagen hair is desired. Also provided is a method of reducing the shedding of hair in a human comprised of applying an effective amount of an azole or zinc pyrithione to an area of a human where such a reduction is desired. Further provided is a method of increasing the diameter of a hair shaft comprising topically applying an effective amount of an azole to an area of a human where an increase in the diameter is desired.

41 Claims, 4 Drawing Sheets

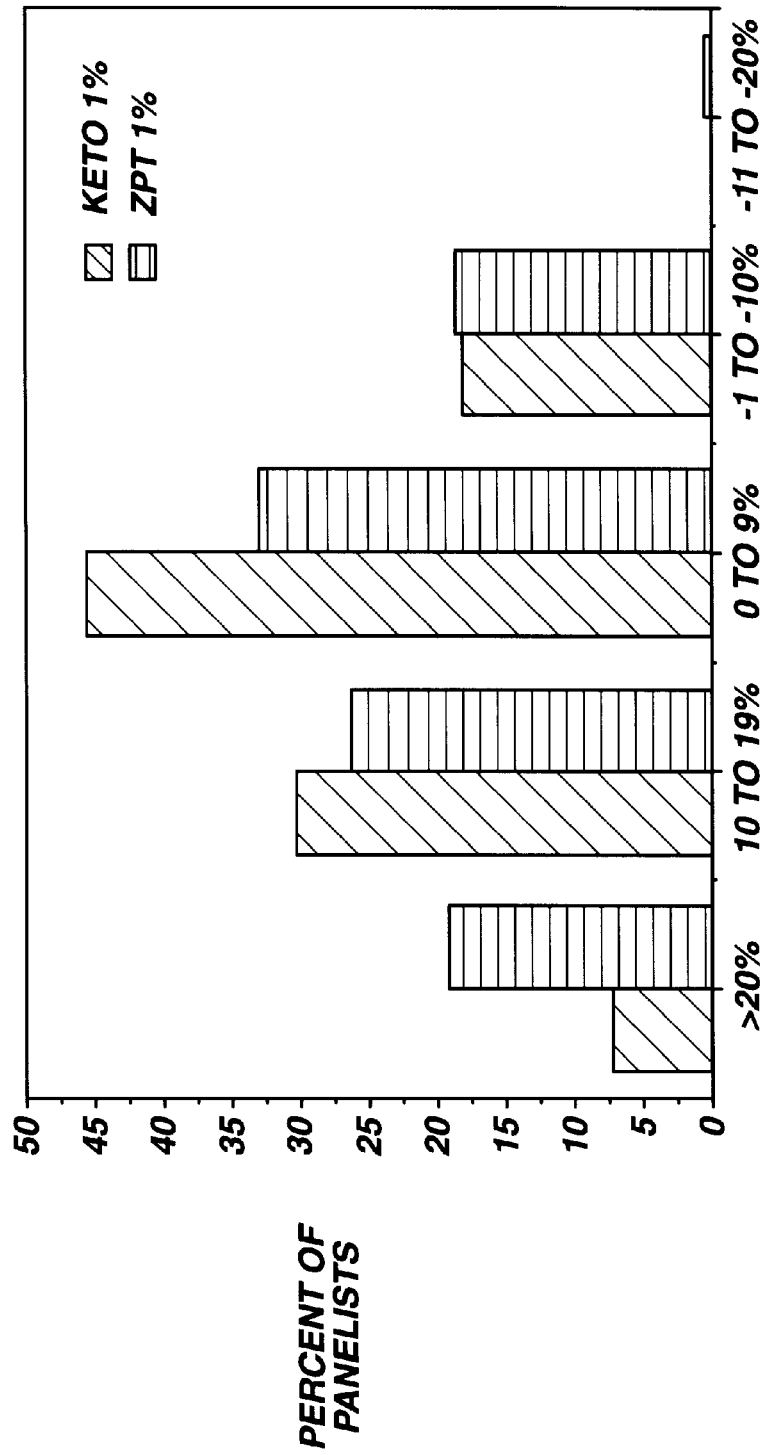

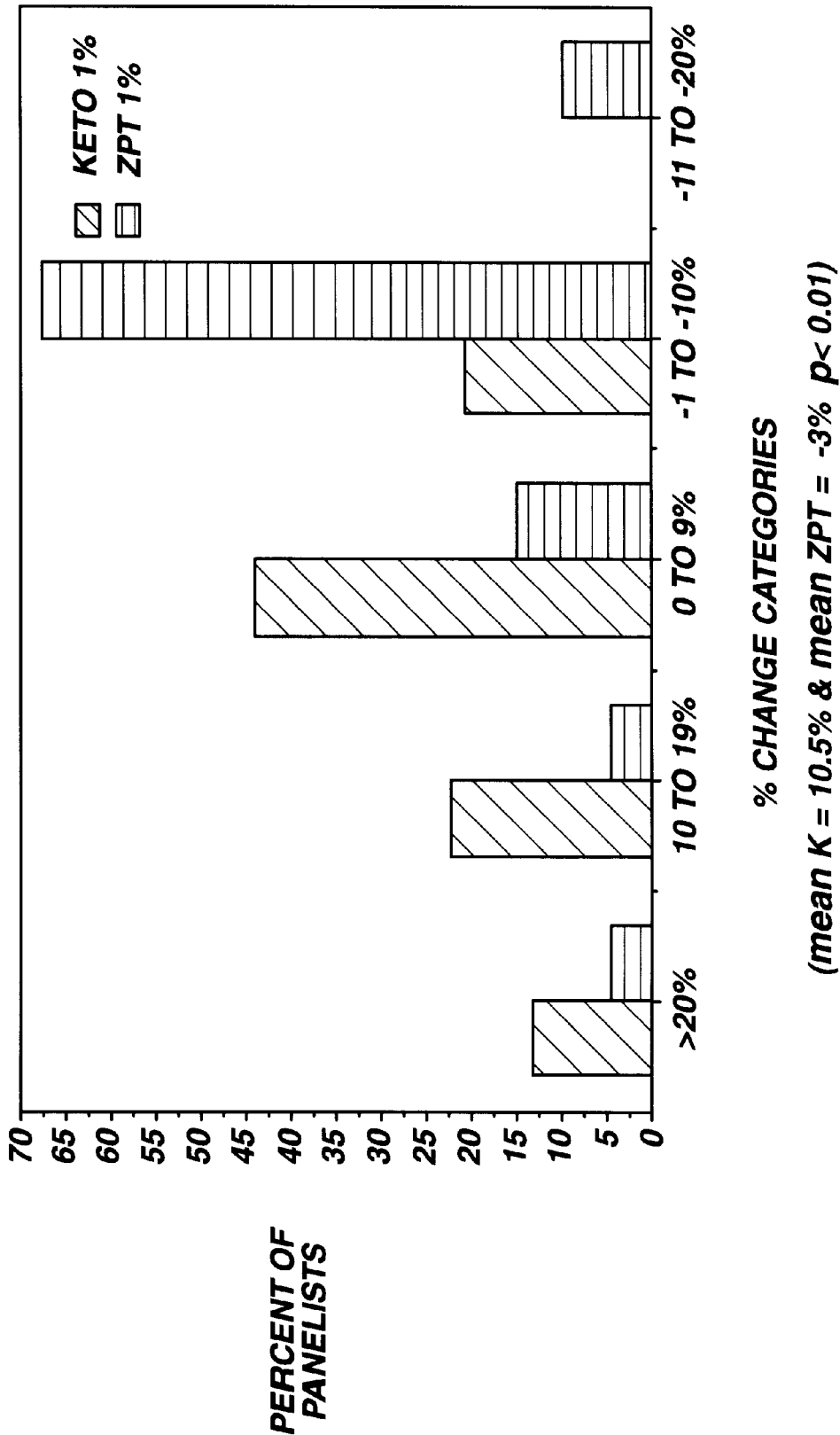

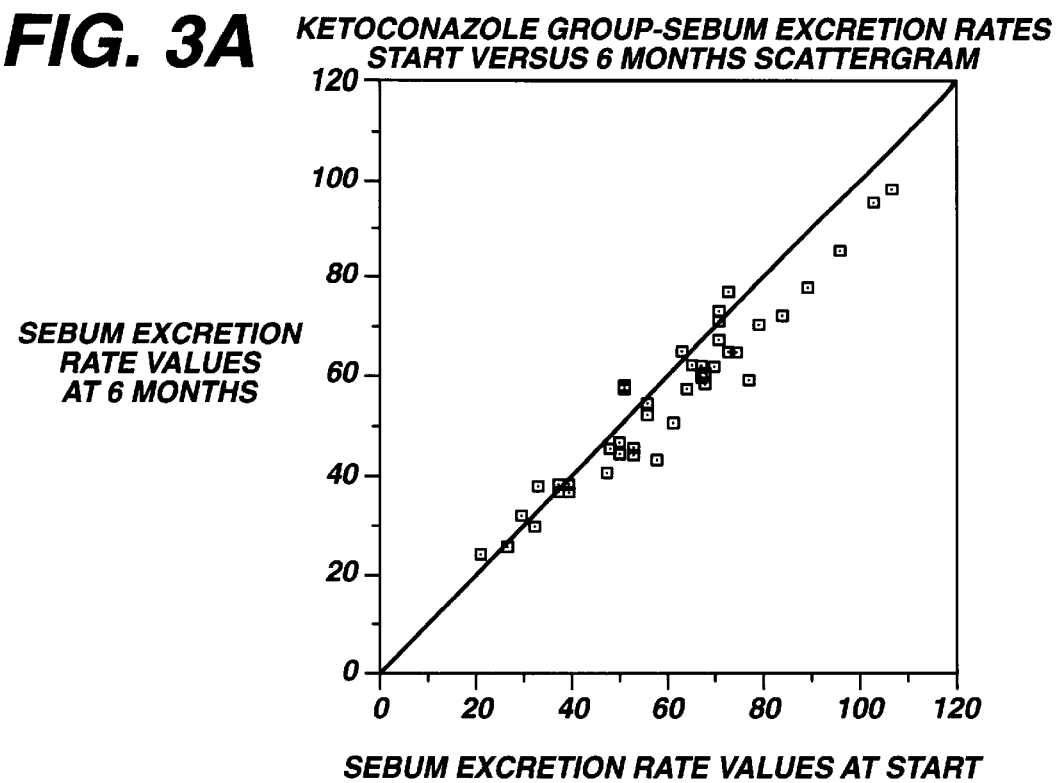
FIG. 3A KETOCONAZOLE GROUP-SEBUM EXCRETION RATES START VERSUS 6 MONTHS SCATTERGRAM
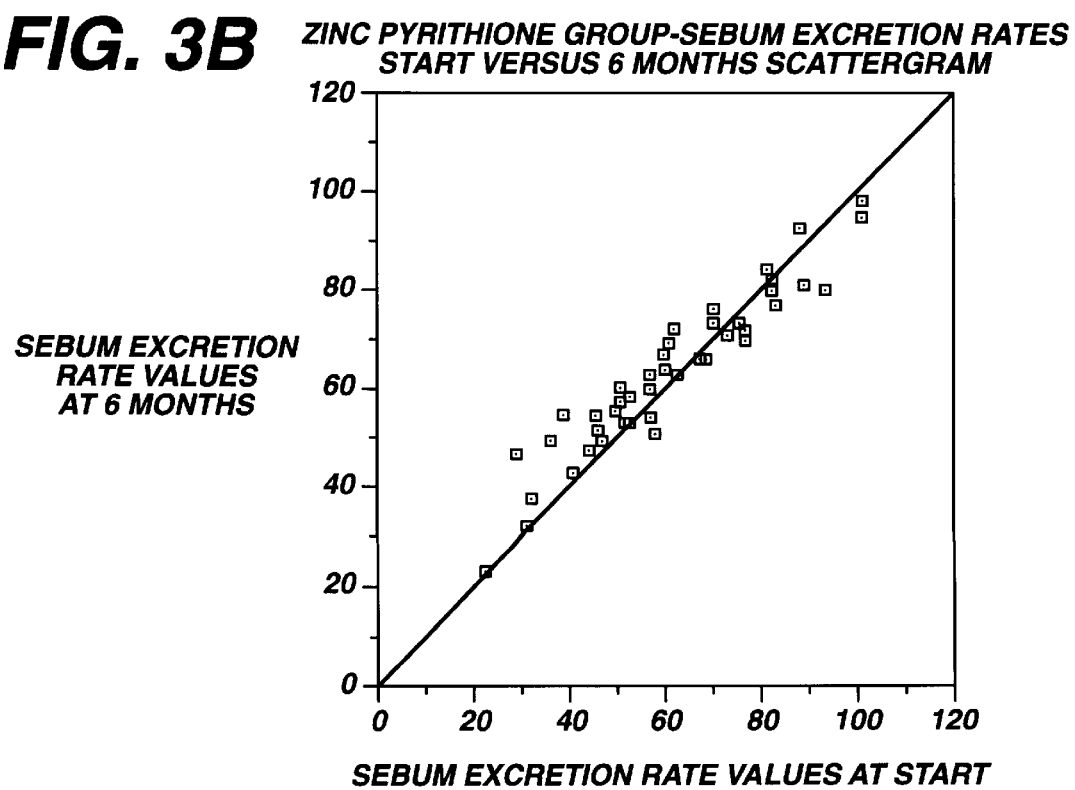
FIG. 3B ZINC PYRITHIONE GROUP-SEBUM EXCRETION RATES START VERSUS 6 MONTHS SCATTERGRAM

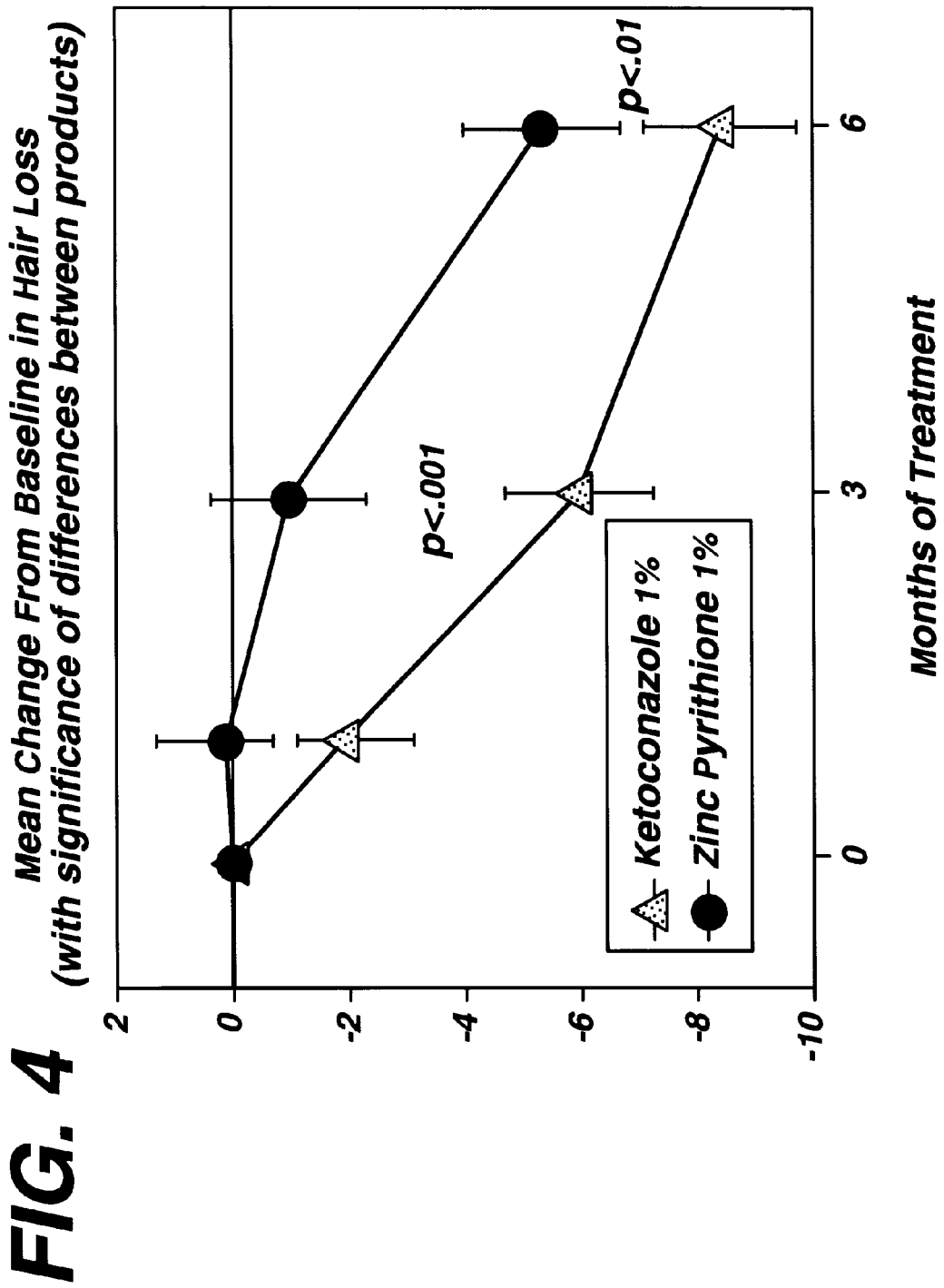

METHODS FOR IMPROVING THE HEALTH OF HAIR AND SCALP

CROSS-REFERENCE TO RELATED APPLICATION

This Application claims the benefit of U.S. Provisional Application No. 60/069,993 filed on Dec. 18, 1997, which is incorporated by reference in its entirety.

BACKGROUND OF THE INVENTION

1. Field of the Invention

The present invention relates to methods of improving the health of hair and the scalp. More particularly, this invention relates to methods for reducing hair shedding, methods for increasing hair diameter, and methods for maintaining hair in the anagen phase for a prolonged period of time.

2. Description of Prior Art

Dandruff ("pityriasis capitis sicca") and seborrheic dermatitis ("pityriasis capitis oleosa") are two related clinical manifestations of one common dermatological disorder that involves the scalp as well as other areas of the body having a high density of sebaceous glands. While dandruff is primarily a scaling condition, it is often also associated with some inflammation. See e.g. Dawber, P., "The Scaly and Itchy Scalp," *Hair and Scalp Disorders* 191–227 (1995). Typically dandruff is expressed on the scalp, but other areas of the body that are predisposed to seborrheic dermatitis also often show mild scaling without obvious signs of inflammation. In seborrheic dermatitis, the inflammatory counterpart of the same disorder, erythema is always present, and the inflammatory infiltrate is more pronounced. See e.g. Ford, G. P., et al., 111 Br. J. Dermatol 603–07 (1984) ("Ford").

Those of skill in the art have come to the consensus that both dandruff and seborrheic dermatitis are two aspects of the same disease. See Ford; Sabouraud, R., "Maladies Due Cuir Chevelu II," Les Maladies Desquamatives, 207–327 (1904); and Van Vloten, W., et al., "Eczeem," 8 Dermatologie and Venereologie 90–109 (1996). It is well known that individuals who have dandruff will, if the condition is not treated, often develop the more inflammatory aspect—seborrheic dermatitis, while those having seborrheic dermatitis might show scaling only during the periods of less pronounced inflammation. Although those skilled in the art generally agree that the lipophylic yeast, *Pityrosporum ovale* ("*P. ovale*"), is a key contributor in the pathogenesis of seborrheic dermatitis and dandruff, it is likewise accepted that both conditions should not be regarded as an infection. Rather, it is the yeast's overcolonization of the scalp and other body areas having a high density of sebaceous glands that causes a very mild inflammatory reaction, i.e. dandruff, or a moderate inflammatory reaction, i.e. seborrheic dermatitis, redness, as well as an accelerated turnover of the epidermis. See Ford and Arese, J., et al., "Effect of Ketoconazole Medicated Shampoos on Squamometry and *Malassezia Ovalis* Load in *Pityriasis Capitis*," 58 Cutis 235–37 (1996).

Typical primary symptoms of dandruff and seborrheic dermatitis include scaling, redness, and itching; however, several other clinical manifestations such as seborrhea (oiliness), telogen effluvium (shedding), thin shaft diameter, androgenic alopecia, and reduction in percent anagen hairs have also been reported in conjunction with this disorder. See Shuster, S., "Psoriatic Alopecia," 87 Br. J. Dermatol. 74–77 (1972); Rushton, D. H., et al., "Natural Progression of Male Pattern Baldness in Young Men," 16 Clin. Exp. Dermatol. 188–192 (1991); Bergfeld, F. W., "Hair Disorders" Dermatology 1541–1560 (1992); and Pierard-Franchimont, C., et al., "Approche Physiopathologique de la Seborrhee Du Cuir Chevelu," 115 Ann. Dermatol. Venereol. 451–53 (1988).

Various methods have been employed to stimulate the growth of hair and/or increase its diameter; however, these methods are not without their shortcomings. One known method employs the application of minoxidil to areas such as the scalp for purposes for stimulating hair growth and prolonging the period of time that hair is in the anagen phase. Unfortunately, this method has been found to be effective in only a small proportion of users. Another known method for increasing hair diameter involves the application of silicone-containing treatments to areas such as the scalp. Disadvantageously, this method produces a "build-up" of silicone on the hair that tends to dull its physical appearance.

It would be desirable to provide a method of treating seborrhigic dermatitis and dandruff by improving these alternative manifestations indicative of an unhealthy scalp.

SUMMARY OF THE INVENTION

In accordance with this invention, there is provided a method of increasing the amount of anagen hair in a human comprising, consisting essentially of, and/or consisting of applying an effective amount of an agent which inhibits the growth of *P. ovale* or a mixture thereof to an area of a human where an increase in the amount of anagen hair is desired.

In another embodiment of this invention, there is provided a method of reducing the shedding of hair in a human comprising, consisting essentially of, and/or consisting of topically applying an effective amount of an agent which inhibits the growth of *P. ovale* or a mixture thereof to an area of the human where a decrease in the shedding is desired.

In yet another embodiment of this invention, there is provided a method of increasing the diameter of a hair shaft comprising, consisting essentially of, and/or consisting of topically applying an effective amount of an imidazole, a triazole, selenium sulfide, a lithium-containing product, or mixtures thereof to an area of a human wherein an increase in the diameter is desired.

The methods of this invention not only are effective in alleviating symptoms indicative of unhealthy hair and scalp, but also are effective in treating two underlying, related clinical manifestations, dandruff and seborrheic dermatitis.

BRIEF DESCRIPTION OF THE DRAWINGS

The invention will be more fully understood and further advantages will be come apparent when reference is made to the following detailed description of the invention and the accompanying drawings in which:

FIG. 1 is a graph of the percent change in amount of anagen hair from baseline in a 6 month period versus the amount of panelists.

FIG. 2 is a graph of the percent change in hair diameter from baseline in a 6 month period versus the amount of panelists.

FIG. 3 is a scattergram of the baseline sebum excretion rate ($\mu g/cm^2/hr$) versus the sebum excretion rate ($\mu g/cm^2/hr$) six months later for subjects using a ketoconazole-containing shampoo (FIG. 3A) and a zinc pyrithione shampoo (FIG. 3B).

FIG. 4 is a graph of the percent change in hair loss reduction from baseline versus the length of treatment from baseline at one, three and six month intervals.

DESCRIPTION OF THE PREFERRED EMBODIMENTS

As used herein, "anagen hair" shall mean hair that is in the growth phase.

In all embodiments of the present invention, the active ingredients may be applied to a desired area via any inert vehicle or carrier suitable for topical applications including, but not limited to a shampoo, a soap, a gel, a cream, a lotion, a solution, and the like (hereinafter collectively "Medium"). The Medium, which can either be oil-based or preferably water-based, may be designed to be left on the skin and not washed shortly after application. In an alternative, preferred embodiment, the Medium may be designed to be rinsed off within a given amount of time after application. In the latter embodiment wherein the active ingredients are incorporated into a shampoo, the shampoo is applied to wet hair, and the hair is washed in accordance with known practices.

The areas to which the active ingredients may be applied include one or more of those areas typically affected by seborrheic dermatitis and dandruff, which include but are not limited to the scalp and other hairy areas, body folds, behind the ears, areas of the body having a high density of sebaceous glands, and/or areas having an increased presence of *P. ovale*.

In the first embodiment of this invention, an anagen hair-inducing agent is comprised of any agent capable of inhibiting the growth of *P. ovale*. Examples of suitable anagen hair-inducing agents include, but are not limited to, imidazoles, triazoles, zinc pyrithione (including zinc pyrithione in its ultramicronized form), selenium sulfide, lithium-containing products such as lithium salts including but not limited to lithium succinate, or mixtures thereof, which are topically applied in an effective amount to an area of a human where an increase in the amount of anagen hair is desired. Preferred areas include those which possess or had possessed hair such as, for example, the scalp.

While various imidazoles may be employed, the preferred compounds include, but are not limited to ketoconazole; dichlorophenyl imidazolodioxalan, which is commercially available from Janssen Pharmaceutica, N.V., under the tradename, "Elubiol"; clotrimazole; itraconazole; miconazole; climbazole; tioconazole; sulconazole; butoconazole; fluconazole; and any possible stereo isomers thereof and mixtures thereof. Ketoconazole and ultra-micronized zinc pyrithione are preferred anagen hair-inducing agents.

The topical application of the anagen hair-inducing agent is performed by applying a dilute solution of the anagen hair-inducing agent to a desired area. The amount of anagen hair-inducing agent used in this embodiment shall be an amount effective for increasing the amount of anagen hair in a desired area of a human. As used herein "amount effective" shall mean an amount sufficient to cover the region of skin surface where an indication exists as well as to ameliorate the indication. Although the amount of anagen hair-inducing agent used will depend upon, for example, the amount of anagen hair desired and a human's tolerance and/or receptiveness to the particular anagen hair-inducing agent selected, typically from about 0.001 mg/sq. mm to about 1000 mg/sq. mm, and preferably from about 0.1 mg/sq. mm to about 50 mg/sq. mm of anagen hair-inducing agent is typically applied to the skin's surface. Such appropriate amounts of anagen hair-inducing agent may be delivered to a desired area when the amount of the anagen hair-inducing agent is present in the desired Medium in an amount, based upon the total weight of the Medium, of from about 0.01 percent to about 20 percent, and preferably from about 0.5 percent to about 5 percent.

The anagen hair-inducing agent is preferably applied topically to the desired areas of the body at regular intervals, and more preferably from about 1 to about 7 times per week. In one embodiment, the anagen hair-inducing agent may be applied more frequently during the initial stages of treatment, e.g. from about 4 to about 7 times per week until the desired effect is achieved, then less frequently when maintenance is desired, e.g. from about 1 to about 2 times per week. It is preferable to continue use of the agent in order to maintain the resulting increase in amount of anagen hair, that is to keep the hair growing for a longer period of time.

The anagen hair-inducing agent should remain on the desired area of the human at least for about 15 seconds, preferably from about 15 seconds to about 5 minutes, and more preferably from about 60 seconds to about 3 minutes.

Media containing the anagen hair-inducing agent may be prepared by combining the anagen hair-inducing agent with the other components commonly present in the Media under ambient conditions via any mixing devices commonly used in the art. When ketoconazole is used as the anagen hair-inducing agent, it is preferable to incorporate an antioxidant component in the Media as set forth in U.S. Pat. No. 5,456,851, which is incorporated by reference herein. Butylated hydroxytoluene (BHT) and butylated hydroxyanisole (BHA) are the antioxidants of choice. Details of how to prepare a cream containing the anagen hair-inducing compound are disclosed in U.S. Pat. No. 4,942,162, which is incorporated by reference herein, and details of how to prepare a shampoo containing the anagen hair-inducing compound are disclosed in U.S. Pat. No. 5,456,851.

In another aspect of the present invention, a hair shedding reductant comprised of any agent capable of inhibiting the growth of *P. ovale* is topically applied in an effective amount to an area of a human where a decrease in the amount of hair shedding is desired. Preferred areas include those which possess hair such as, for example, the scalp. Examples of suitable hair shedding reductants include, but are not limited to, imidazoles, triazoles, elubiol, zinc pyrithione (including zinc pyrithione in its ultramicronized form), selenium sulfide, lithium-containing products such as lithium salts including but not limited to lithium succinate, or mixtures thereof.

Examples of suitable imidazoles include, but are not limited to those set forth above. Ketoconazole and ultra-micronized zinc pyrithione are preferred hair shedding reductant agents.

The amount of hair shedding reductant used in this embodiment shall be an amount effective for decreasing the amount of shedding hair in a desired area of the human. This amount, as well as the method for preparing the Media containing the hair shedding reductant and the method for using such Media are similar to those respective amounts and methods provided above for the Media containing the anagen hair-inducing agent.

In another aspect of the present invention, a hair diameter increasing agent comprised of imidazoles, triazoles, selenium sulfide, lithium-containing products such as lithium salts including but not limited to lithium succinate, or mixtures thereof (including mixtures with zinc pyrithione) is topically applied in an effective amount to an area of a human where in an increase in hair diameter is desired. Preferred areas include those which possess hair such as, for example, the scalp.

Examples of suitable imidazoles include, but are not limited to those set forth above. Ketoconazole is the preferred hair diameter increasing agent. In embodiments wherein zinc pyrithione is used in combination with a hair diameter increasing agent, the zinc pyrithione is present in an amount, based upon the total weight of the solution comprised of the hair diameter increasing agent, of from about 0.25 percent to about 2 percent.

The amount of hair diameter increasing agent used in this embodiment shall be an amount effective for increasing the diameter of hair shafts in a desired area of the human. This amount, as well as the method for preparing the Media containing the hair diameter increasing agent and the method for using such Media are similar to those respective amounts and methods provided above for the Media containing the anagen hair-inducing agent.

In nearly all embodiments of the present invention, positive results were apparent as early as about 2 weeks after the first use. However, after using the anagen hair inducing agent for about 6 months in accordance with the process of the present invention, we have unexpectedly found that the number of anagen hairs in the treated area increased by a percentage of up to about 40 percent. Further, we have also unexpectedly found that the number of hairs shed in the treated area after 6 months of use of the hair shedding reductant in accordance with the process of this invention decreased by a percentage of up to about 20 percent.

In addition, we have unexpectedly found that after using the hair diameter increasing agent for about 6 months in accordance with the process of the present invention, the diameter of the hair shafts in the treated area increased by up to a percentage of about 50 percent. Similarly, we have found that the oiliness of these treated areas also decreased by about 9% during this period. In view of these results, we have discovered a correlation between sebum excretion rate and hair diameter, i.e. that those who experienced a greater than 20% increase in hair diameter also experience about a 6% decrease in sebum excretion rate. Conversely, those who did not use the hair diameter increasing agent and who experienced about a 5% decrease in hair diameter also had about a 20% increase in scalp oiliness. We believe that the use of products which are capable of reducing the oil of the treated area, e.g. scalp, will also enhance the thickness of hair when used on a regular basis.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

The following shampoos were used in the Examples below:

Shampoo A: a 1% ketoconazole shampoo available from Neutrogena Corporation under the tradename, "Long Lasting Dandruff Shampoo."

Shampoo B: a 1% zinc pyrithione shampoo available from the Procter & Gamble Company under the tradename, "New Head & Shoulders."

The following test methods were performed in the Examples below:

1) Pilary Index (% $\mu$m): The pilary index was calculated as the product of the percent of anagen hair and the hair shaft diameter ($\mu$m).

For the baseline assessment, hair samples were identified on the vertex area then plucked out with a rubber-tipped tweezer. The removed hair sample was placed under a microscope in order to count the hair strands and to identify the hair cycle stage for each respective strand, i.e. anagen (growing), telogen (ending), or catagen (resting). From these resulting trichograms the proportion of hairs in the anagen phase was obtained.

A computerized image analysis of the same hair samples was performed using a MOP Videoplan analyzer manufactured by Kontron GmbH in order to measure the average diameter of the hair shafts in accordance with the directions provided therewith.

By using a 3-point midline and facial coordinate system with nose tip, ear and fontanelle coordinates, precise relocation of the sample site was achieved for measurements taken after the baseline assessment.

2) Hair shedding: The amount of hairs shed was evaluated by a semi-luantitative count of the hairs collected immediately after the last shampoo usage by the subject, which typically was about 24 hours before a subject visited the laboratory for evaluation. The hairs were collected in a small transparent envelope and then compared with a series of similar reference envelopes kept at the laboratory. Each reference envelope contained a multiple of 10 hairs. The number of hairs shed in the subject's envelope was matched to a reference standard.

3) Sebum excretion ($\mu$g/cm$^2$/hour): A sample site near the hairline was located using the above 3-point midline and facial coordinate system. One hour after cleaning the skin of the site with a 70% ethanol solution, the amount of sebum excreted at that area was measured by holding a probe of a computerized Model SM810 Courage sebumeter from Khazaka, (GmbH to the site until an excretion value was provided on the sebumeter.

Using the above-mentioned 3-point system, precise relocation of the sample site was achieved for measurements taken after the baseline assessment.

Example 1

Comparative Testing: Percent Hairs in Anagen Phase

Forty-four adult males who ranged in age from 18 to 65 years old, had mild to moderate dandruff, and had mild androgenic alopecia of the vertex, were assigned to shampoo 2 to 3 times per week with Shampoo A, and forty-three other males having the same characteristics were similarly assigned to shampoo with Shampoo B. Before beginning to shampoo with their assigned shampoo, the baseline pilary index value was calculated for each male. After 6 months of shampooing according to this regime, the pilary index value for each male was recalculated.

As evidenced in Table 1 below and in FIG. 1, both the ketoconazole-containing shampoo and the zinc pyrithione-containing shampoo beneficially improved the percent of anagen hairs by 8.3% and 10.3%, respectively.

TABLE 1

EFFECT OF KETOCONAZOLE AND ZINC PYRITHIONE ON PERCENT HAIRS IN ANAGEN PHASE

| CHANGE IN AMOUNT OF ANAGEN HAIRS (%) | KETOCONAZOLE N = 44 | ZINC PYRITHIONE N = 43 |
|---|---|---|
| >20 | 3 | 8 |
| 10 to 19 | 13 | 11 |
| 0 to 9 | 20 | 14 |

TABLE 1-continued

EFFECT OF KETOCONAZOLE AND ZINC PYRITHIONE
ON PERCENT HAIRS IN ANAGEN PHASE

| CHANGE IN AMOUNT OF ANAGEN HAIRS (%) | KETOCONAZOLE N = 44 | ZINC PYRITHIONE N = 43 |
|---|---|---|
| −1 to −10* | 8 | 8 |
| −11 to −20* | 0 | 2 |

*a negative value reflects a decrease in the amount of hairs in anagen phase

This Example shows that ketoconazole and zinc pyrithione are effective in increasing the number of anagen hairs, i.e. in keeping the hair growing for a longer period of time.

Example 2

Comparative Testing: Change in Hair Diameter

Example 1 was repeated but the baseline and 6 month values for hair diameter were measured.

As evidenced in Table 2 and in FIG. 2, the ketoconazole-containing shampoo beneficially increased the hair shaft diameter by about 11%, whereas the diameter was slightly decreased by about 3% in those subjects using the zinc pyrithione-containing shampoo.

TABLE 2

EFFECT OF KETOCONAZOLE AND ZINC PYRITHIONE
ON CHANGE IN HAIR DIAMETER

| CHANGE IN HAIR DIAMETER (%) | KETOCONAZOLE N = 44 | ZINC PYRITHIONE N = 43 |
|---|---|---|
| >20 | 6 | 2 |
| 10 to 19 | 10 | 2 |
| 0 to 9 | 19 | 6 |
| −1 to −10** | 9 | 29 |
| −11 to −20** | 0 | 4 |

**a negative value reflects a decrease in the hair diameter

This Example shows that ketoconazole, as opposed to zinc pyrithione, is more effective in increasing the diameter of a hair shaft.

Example 3

Comparative Testing: Change in Sebum Excretion Rate

Example 2 was repeated, except the baseline and 6 month sebum excretion rate was measured.

As evidenced in FIG. 3A and FIG. 3B, the sebum excretion rate for those subjects using the ketoconazole-containing shampoo decreased over the 6 month period by about 6%, while the sebum excretion rate for those subjects using the zinc pyrithione-containing shampoo increased by about 7%. Since this correlation addressed two biological parameters in relation to each other, the correlation is apparent independent from the type of shampoo used as illustrated in Table 3 and Table 4 below, which shows that the greater the reduction in the amount of sebum excretion, the greater the change in hair diameter.

TABLE 3

CHANGES IN HAIR DIAMETER IN RELATION TO
SCALP OIL CHANGE (CATEGORIES INDEPENDENT
FROM TYPE OF SHAMPOO USED)

| CATEGORY: CHANGE IN SCALP OILINESS (%) | MEAN CHANGE IN HAIR DIAMETER (%) |
|---|---|
| >10 DECREASE (Mean = 14.4) | +11 |
| from 5 DECREASE TO 5 INCREASE (Mean = −.6) | 3.7 |
| >10 INCREASE | −3.6*** |

***a negative value reflects a decrease in hair diameter

TABLE 4

CHANGES IN SCALP OILINESS IN RELATION
TO HAIR DIAMETER CHANGE
(CATEGORIES INDEPENDENT FROM TYPE OF
SHAMPOO USED)

| CATEGORY: CHANGE IN HAIR DIAMETER (%) | MEAN CHANGE IN SCALP OIL (%) |
|---|---|
| >20 INCREASE (Mean = 30.5) | −6.25**** |
| FROM 10 TO 19 INCREASE (Mean = 13.6) | −2.2**** |
| FROM −4 TO 9 (Mean = .7) | |
| FROM 5 TO 10 DECREASE (Mean = −6.4) | 5.4 |
| >10% DECREASE (Mean = −12) | .6 |

****a negative value reflects a decrease in the amount of oil produced

This Example shows that ketoconazole is effective in both reducing the amount of sebum excretion while also increasing the diameter of hair shafts. By contrast, zinc pyrithione is comparatively less effective in reducing the amount of sebum excreted and further appears to contribute to a decrease in the diameter of hair shafts. Thus, the Example suggests a relationship between reducing the production of sebum in order to increase hair diameter.

Example 4

Comparative Testing: Hair Shedding

Fifty males who ranged in age from 26 to 56 years old, had mild to moderate dandruff, and had mild androgenic alopecia of the vertex were assigned to shampoo 2 to 3 times per week with Shampoo A, and fifty other males having the same characteristics were similarly assigned to shampoo with Shampoo B.

Before beginning to shampoo with their assigned shampoo, the baseline shedding value was calculated for each male. At baseline, about ⅓ of the subjects in both groups had low hair loss, i.e. about 20 to about 30 shafts, ⅓ of the subjects had moderate hair loss, i.e. about 30 to about 40 shafts, and ⅓ of the subjects had high hair loss, i.e. more than about 40 shafts.

After 1, 3, and 6 months of shampooing according to this regime, the shedding value for each male was recalculated. As illustrated in FIG. 4, the subjects who used the ketoconazole shampoo exhibited a significant reduction in hair loss in after only one month of treatment, and a highly significant reduction after three and six months of treatment. At six months of treatment, both groups exhibited significant reductions from base line levels of hair loss.

As further illustrated in Table 5 below, we found that the change in hair loss at six months was related to the baseline hair loss measurement:

TABLE 5

Six Month Change in Hair Loss

| Degree of Hair Loss of Subjects (Baseline) | Reduction in Hair Loss from Baseline by Subjects Using Ketoconazole Shampoo A (%) | Reduction in Hair Loss from Baseline by Subjects Using Zinc Pyrithione Shampoo B (%) |
| --- | --- | --- |
| Low | 1 | −2 |
| Moderate | 9 | 6 |
| High | 17 | 9 |

At baseline, the degree of hair loss in the two groups was nearly identical. However, Table 5 shows that as the degree of baseline hair loss was increased, the difference in the reduction of hair loss at six months became more pronounced. Moreover, of those participants who dropped out of the study, 4 of the 6 dropouts in the group using Shampoo A had high baseline levels of hair loss, while 5 of the 7 dropouts in the group using Shampoo B had low baseline levels of hair loss. Therefore, the group using Shampoo A lost subjects expected to have a superior result, while the group using Shampoo B lost subjects who were expected to have a relatively low improvement in hair loss reduction.

Although this Example shows that ketoconazole and zinc pyrithione are both effective in hair loss reduction, it is apparent that ketoconazole is the preferred agent for hair loss reduction. This Example also shows that the improvement in hair loss reduction occurs relatively soon after using ketoconazole. Further, this Example shows that the reduction in hair loss is more dramatic in those subjects exhibiting a relatively excessive hair loss before treatment.

While preferred embodiments have been described in the foregoing detailed description, it will be recognized that there is no intent to limit the invention by such disclosure, but rather it is intended to cover all modifications and variations falling within the spirit and scope of the invention as defined in the appended claims.

What is claimed is:

1. A method of increasing the amount of time during which hair in a human remains in an anagen state comprised of topically applying an effective amount of an agent which inhibits the growth of *P. ovale* or mixture thereof to an area of the human wherein an increase in the amount of anagen hair is desired.

2. The method of claim 1 wherein the agent is comprised of an imidazole, a triazole, zinc pyrithione, selenium sulfide, a lithium-containing product, or mixtures thereof.

3. The method of claim 1 wherein the imidazole is ketoconazole; dichlorophenyl imidazolodioxalan; clotrimazole; itraconazole; miconazole; climbazole; tioconazole; sulconazole; butoconazole; fluconazole; or any possible stereo isomers thereof and mixtures thereof.

4. The method of claim 1 wherein the agent is ketoconazole, zinc pyrithione, or mixtures thereof.

5. The method of claim 1 wherein the anagen hair inducing agent is topically applied in an amount of from about 0.001 mg/sq. mm to about 1000 mg/sq. mm to the area.

6. The method of claim 1 wherein the anagen hair inducing agent is applied in a water-based medium or an oil-based medium.

7. The method of claim 6 wherein the medium is water-based.

8. The method of claim 6 wherein the medium contains, based upon the total weight of the medium, from about 0.01 percent to about 20 percent anagen hair inducing agent.

9. The method of claim 6 wherein the medium contains, based upon the total weight of the medium, from about 0.5 percent to about 5 percent anagen hair inducing agent.

10. The method of claim 6 wherein the medium is a cream.

11. The method of claim 5 wherein the medium is a shampoo.

12. The method of claim 1 wherein the anagen hair inducing agent is applied from about 1 to about 7 times per week.

13. A method of reducing the shedding of hair in a human comprised of topically applying an effective amount of an agent which inhibits the growth of *P. ovale* or mixture thereof to an area of the human wherein a decrease in the amount of shedding is desired.

14. The method of claim 13 wherein the agent is comprised of an imidazole, a triazole, zinc pyrithione, selenium sulfide, a lithium-containing product, or mixtures thereof.

15. The method of claim 13 wherein the imidazole is ketoconazole; dichlorophenyl imidazolodioxalan; clotrimazole; itraconazole; miconazole; climbazole; tioconazole; sulconazole; butoconazole; fluconazole; or any possible stereo isomers thereof and mixtures thereof.

16. The method of claim 13 wherein the agent is ketoconazole, zinc pyrithione, or mixtures thereof.

17. The method of claim 13 wherein the hair shedding reductant is topically applied in an amount of from about 0.001 mg/sq. mm to about 1000 mg/sq. mm to the area.

18. The method of claim 13 wherein the hair shedding reductant is applied in a water-based medium or an oil-based medium.

19. The method of claim 18 wherein the medium is a water-based medium.

20. The method of claim 18 wherein the medium contains, based upon the total weight of the medium, from about 0.01 percent to about 20 percent hair shedding reductant.

21. The method of claim 20 wherein the medium contains, based upon the total weight of the medium, from about 0.5 percent to about 5 percent hair shedding reductant.

22. The method of claim 18 wherein the medium is a cream.

23. The method of claim 18 wherein the medium is a shampoo.

24. The method of claim 13 wherein the hair shedding reductant is applied from about 1 to about 7 times per week.

25. A method of increasing the diameter of a hair shaft in a human comprised of topically applying an effective amount of a hair diameter increasing agent
   a) comprised of selenium sulfide, lithium-containing product or mixtures thereof;
   b) consisting essentially of an imidazole, a triazole, and mixtures thereof; and
   c) mixtures thereof
to an area of the human wherein a decrease in the amount of shedding is desired.

26. The method of claim 25 wherein the imidazole is ketoconazole, elubiol, or mixtures thereof.

27. The method of claim 25 wherein the hair diameter increasing agent is topically applied in an amount of from about 0.001 mg/sq. mm to about 1000 mg/sq. mm to the area.

28. The method of claim 25 wherein the hair diameter increasing agent is applied in a water-based medium or an oil-based medium.

29. The method of claim 28 wherein the medium is a water-based medium.

30. The method of claim 28 wherein the medium contains, based upon the total weight of the medium, from about 0.01 percent to about 20 percent hair diameter increasing agent.

31. The method of claim 28 wherein the medium contains, based upon the total weight of the medium, from about 0.5 percent to about 5 percent hair diameter increasing agent.

32. The method of claim 28 wherein the medium is a cream.

33. The method of claim 29 wherein the medium is a shampoo.

34. The method of claim 25 wherein the hair diameter increasing agent is applied from about 1 to about 7 times per week.

35. The method of claim 25 wherein said hair diameter increasing agent is combined with zinc pyrithione.

36. A method for increasing the thickness of hair in humans comprising topically applying an oil reducing agent to a desired area.

37. The method of claim 36 wherein the agent is applied in an oil-based or a water-based medium.

38. The method of claim 37 wherein the medium is in the form of a shampoo.

39. The method of claim 37 wherein the medium is in the form of a cream.

40. A method for increasing the period of time during which hair grows in a human comprised of topically applying an effective amount of an agent which inhibits the growth of *P. ovale* or mixture thereof to a desired area of the human.

41. A method of increasing the diameter of a hair shaft in a human comprised of topically applying an effective amount of a hair diameter increasing agent comprised of
- a) an imidazole selected from the group consisting of ketoconazole, dichlorophenyl imidazolodioxalan, clotrimazole, itraconazole, miconoazole, climbazole, tioconazole, sulconazole, butoconazole, fluconzaole, and stereo isomers and mixtures thereof;
- b) selenium sulfide;
- c) lithium-containing product; or
- d) mixtures thereof to an area of the human wherein a decrease in the amount of shedding is desired.

* * * * *

(12) REEXAMINATION CERTIFICATE (4769th)
United States Patent
Cauwenbergh

(10) Number: US 6,099,870 C1
(45) Certificate Issued: *Apr. 15, 2003

(54) METHODS FOR IMPROVING THE HEALTH OF HAIR AND SCALP

(75) Inventor: Gerard F. Cauwenbergh, Plainsboro, NJ (US)

(73) Assignee: Johnson & Johnson Consumer Companies, Inc., Skillman, NJ (US)

( * ) Notice: This patent issued on a continued prosecution application filed under 37 CFR 1.53(d), and is subject to the twenty year patent term provisions of 35 U.S.C. 154(a)(2).

Reexamination Request:
No. 90/006,008, May 14, 2001

Reexamination Certificate for:
Patent No.: 6,099,870
Issued: Aug. 8, 2000
Appl. No.: 09/208,948
Filed: Dec. 9, 1998

Related U.S. Application Data

(60) Provisional application No. 60/069,993, filed on Dec. 18, 1997.

(51) Int. Cl.$^7$ ............... A61K 33/04; A61K 33/00; A61K 31/555; A61K 31/415
(52) U.S. Cl. ............... 424/702; 424/722; 514/188; 514/397
(58) Field of Search ............... 424/702, 722; 514/188, 399

(56) References Cited

U.S. PATENT DOCUMENTS

| | | | |
|---|---|---|---|
| 4,335,125 A | 6/1982 | Heeres et al. | 424/250 |
| 4,569,935 A | 2/1986 | Rosenberg et al. | 514/252 |
| 4,942,162 A | 7/1990 | Rosenberg et al. | 514/252 |
| 5,204,337 A | 4/1993 | Labrie et al. | 514/182 |
| 5,374,633 A | 12/1994 | Parab | 514/252 |
| 5,476,852 A | 12/1995 | Cauwenbergh | 514/252 |

FOREIGN PATENT DOCUMENTS

| | | |
|---|---|---|
| EP | 0 270 316 | 6/1988 |
| EP | 0396 184 | 11/1990 |
| EP | 0536 182 | 4/1995 |

OTHER PUBLICATIONS

Pierard, U.S. patent application Ser. No. 08/437,472, filed on May 9, 1995.

Carr, M. et al., "Treatment of seborrhoeic dermatitis with ketoconazole: I. Response of seborrhoeic dermatitis of the scalp to topical ketoconazole," *Brit. Jour. of Dermatology*, 1987, (116), 214–216.

Green, C.A., et al., "Treatment of seborrhoeic dermatitis with ketoconazole: II. Response of seborrhoeic dermatitis of the face, scalp and trunk to topical ketoconazole," *Brit. Jour. of Dermatology*, 1987, (116), 217–221.

Piérard, G., "Ketoconazole Shampoo: Past, Present and Future," *Journal d'actualite dermatologiques belges*, 1994, (12), 8–12. (Translation provided).

*Disorders of Hair Growth*, Elise A. Olsen, (ed..) McGraw–Hill, NY, 1994, 258, 275, 278.

*Illustrated Stedman's Medical Dictionary*, 24th Edition, Williams & Wilkins, Baltimore, 1982, 1090.

Embase Abstract 83240235, Hanna, J.M. et al., "Malassezia (pityrosporum) folliculitis occurring with granuloma annulare and alopecia reata," *Arch. Dermatol.*, 1983, (119/10), 869–871.

Kovacs, I. et al., "Usefulness of ketoconazole (nizoral) in the treatment of androgenization symptoms in women suffering concurrently from candidiasis or dermatomycosis," *Ther Hung.*, 1988, (36/4), 174–178.

*Primary Examiner*—Frederick Krass

(57) ABSTRACT

A method of increasing the amount of anagen hair in a human comprising applying an azole or zinc pyrithione, or mixtures thereof to an area of a human where an increase in the amount of anagen hair is desired. Also provided is a method of reducing the shedding of hair in a human comprised of applying an effective amount of an azole or zinc pyrithione to an area of a human where such a reduction is desired. Further provided is a method of increasing the diameter of a hair shaft comprising topically applying an effective amount of an azole to an area of a human where an increase in the diameter is desired.

US 6,099,870 C1

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 13–24 is confirmed.

Claim 2 is cancelled.

Claims 1, 3, 4, 25, 26, 36, 40 and 41 are determined to be patentable as amended.

Claims 5–12, 27–35 and 37–39, dependent on an amended claim, are determined to be patentable.

New claims 42 and 43 are added and determined to be patentable.

1. A method of increasing the amount of time during which hair in a human remains in an anagen state [comprised of], *comprising* topically applying an effective amount of an agent which inhibits the growth of P. ovalae [or mixture thereof] to an area of the human wherein an increase in the amount of anagen hair is desired, *wherein said agent is an imidazole selected from the group consisting of dichlorophenyl imidazolodioxalan, clotrimazole, itraconazole, miconazole, climbazole, tioconazole, sulconazole, butoconazole, fluconazole, any possible stereo isomers thereof and mixtures thereof; or a triazole; zinc pyrithione; selenium sulfide; a lithium-containing product; or mixture thereof.*

3. The method of claim 1 wherein the imidazole is [ketoconazole;] *dichlorophenyl imidazolodioxalan;* [clotrimazole; itraconazole; miconazole; climbazole; tioconazole; sulconazole; butoconazole; fluconazole;] or any possible stereo isomers thereof [and mixtures thereof].

4. The method of claim 1 wherein the agent is [ketoconazole,] zinc pyrithione[, or mixtures thereof].

25. A method of increasing the diameter of a hair shaft in a human comprised of topically applying an effective amount of a hair diameter increasing agent *selected from the group consisting of*

[a) comprised of] selenium sulfide, *a* lithium-containing product, [or mixtures thereof;
b) consisting essentially of an imidazole,] *dichlorophenyl imidazolodioxalan,* a triazole, and mixtures thereof, [; and
c) mixtures thereof]

to an area of the human wherein [a decrease in the amount of shedding] *an increase in the diameter of hair shafts* is desired.

26. The method of claim 25 wherein [the imidazole is ketoconazole, elubiol, or mixtures thereof] *the agent is dichlorophenyl imidazolodioxalan.*

36. A method for increasing the thickness of hair in humans comprising topically applying on oil reducing agent to a desired area *wherein said oil reducing agent is an imidazole selected from the group consisting of dichlorophenyl imidazolodioxalan, clotrimazole, itraconazole, miconazole, climbazole, tioconazole, sulconazole, butoconazole, fluconazole, any possible stereo isomers thereof and mixtures thereof; or a triazole; zinc pyrithione; selenium sulfide; a lithium-containing product; or mixtures thereof.*

40. A method for increasing the period of time during which hair grows in a human [comprised of] *comprising* topically applying an effective amount of an agent which inhibits the growth of P. ovalae [or mixture thereof] to a desired area of the human, *wherein said agent is an imidazole selected from the group consisting of dichlorophenyl imidazolodioxalan, clotrimazole, itraconazole, miconazole, climbazole, tioconazole, sulconazole, butoconazole, fluconazole, any possible stereo isomers thereof and mixtures thereof; or a triazole; zinc pyrithione; selenium sulfide; a lithium-containing product; or mixtures thereof.*

41. A method of increasing the diameter of a hair shaft in a human comprised of topically applying an effective amount of a hair diameter increasing agent comprised of

[a)] an imidazole selected from the group consisting of [ketoconazole,] dichlorophenyl imidazolodioxalan, clotrimazole, itraconazole, miconazole, climbazole, tioconazole, sulconazole, butoconazole, fluconazole, and stereo isomers and mixtures thereof, [;
b) selenium sulfide;
c) lithium-containing product; or
d) mixtures thereof]

to an area of the human wherein [a decrease in the amount of shedding] *an increase in the diameter of the hair shafts* is desired.

42. *A method of increasing the amount of time during which hair in a human remains in an anagen state comprising topically applying an effective amount of an agent which inhibits the growth of P. ovalae to an area of the human wherein an increase in the amount of anagen hair is desired, provided that said growth inhibiting agent comprises other than an effective amount of ketoconazole.*

43. *A method of increasing the diameter of a hair shaft in a human comprised of topically applying an effective amount of a hair diameter increasing agent selected from the group consisting of selenium sulfide, lithium-containing product, an imidazole, a triazole, and mixtures thereof, to an area of the human wherein an increase in the diameter of hair shafts is desired, provided said hair diameter increasing agent comprises other than an effective amount of ketoconazole.*

* * * * *